United States Patent [19]

Bohn

[11] 4,402,872
[45] Sep. 6, 1983

[54] PROTEIN AND PROCESS FOR ISOLATING IT

[75] Inventor: Hans Bohn, Marburg an der Lahn, Fed. Rep. of Germany

[73] Assignee: Behringwerke Aktiengesellschaft, Marburg an der Lahn, Fed. Rep. of Germany

[21] Appl. No.: 357,077

[22] Filed: Mar. 11, 1982

[30] Foreign Application Priority Data

Mar. 13, 1981 [DE] Fed. Rep. of Germany ....... 3109629

[51] Int. Cl.³ .................. C07G 7/00; A61K 35/42; A61K 35/50; A61K 39/395
[52] U.S. Cl. .................. 260/112 R; 260/112 B; 424/85; 424/88; 424/95; 424/101; 424/104; 424/113
[58] Field of Search ............... 260/112 R, 112 B; 424/85, 88

[56] References Cited

U.S. PATENT DOCUMENTS

| 4,217,339 | 8/1980 | Bohn et al. | 260/112 R X |
| 4,254,021 | 3/1981 | Bohn et al. | 260/112 B |
| 4,269,825 | 5/1981 | Bohn et al. | 260/112 R X |
| 4,301,064 | 11/1981 | Bohn | 260/112 R |
| 4,348,316 | 9/1982 | Bohn | 260/112 R |
| 4,368,148 | 1/1983 | Bohn | 260/112 R X |

OTHER PUBLICATIONS

Arch–Gynak, 165–175, (1972), vol. 212, Bohn.

Primary Examiner—Howard E. Schain
Attorney, Agent, or Firm—Curtis, Morris & Safford

[57] ABSTRACT

What are disclosed are an isolated tissue protein, denominated PP16, which can be used to prepare anti-sera useful as diagnostic agents, said protein being found in extracts of some human organs such as the placenta, spleen, stomach, and lung and being capable of isolation therefrom and which has the following properties:

(a) a carbohydrate content of 4.3±1.6%, comprising 3.4±1.2% of hexoses, 0.24±0.07% hexosamines, 0.06±0.03% of fucose, and 0.6±0.3% of neuraminic acid;
(b) a sedimentation coefficient $S_{20,w}^0$ of 4.6±0.4 S;
(c) a molecular weight, determined in a polyacrylamide gel containing sodium dodecyl-sulfate, of 46,000±3,000;
(d) an extinction coefficient $E_1{}_{cm}^{1\%}$ (280 nm) of 8.82±0.5;
(e) an electrophoretic mobility in the range of albumin; and
(f) an isoelectric point of 4.7±0.2.

6 Claims, 1 Drawing Figure

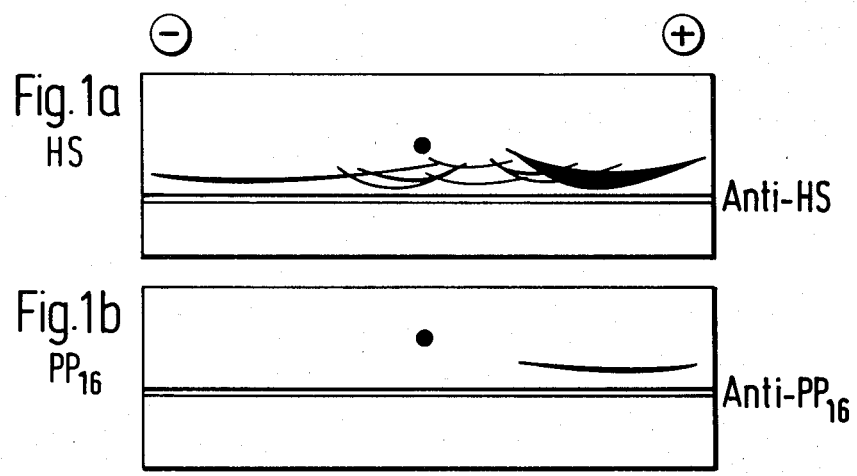

PROTEIN AND PROCESS FOR ISOLATING IT

The present invention relates to a protein, denominated $PP_{16}$, and to methods for isolating, concentrating, and using the same.

Extracts of human organs, and especially placentas, have already been found to contain a number of soluble proteins originating from these tissues (H. Bohn, Placental and Pregnancy Proteins in Carcino-Embryonic Proteins, volume 1., editor: F. G. Lehmann, Elsevier/North-Holland Biomedical Press, 1979).

The present invention describes the isolation and characterization of a new soluble protein, called $PP_{16}$.

$PP_{16}$ occurs in the extract of some human organs, such as the placenta, spleen, stomach and lung. On the average 22 mg of this protein can be extracted from a fully developed human placenta (600 g) with physiological salt solution. The concentration of this protein in the spleen, stomach and lung of adult humans is probably of a similar order. This protein is either absent from extracts of other organs or present in a substantially smaller concentration. $PP_{16}$ is usually also absent or present only in traces ($<1$ mg/l) in the serum and other body fluids of humans.

The invention relates to the protein $PP_{16}$ which has
(a) a carbohydrate content of $4.3\pm1.6\%$, comprising $3.4\pm1.2\%$ of hexoses, $0.24\pm0.07\%$ of hexosamines, $0.06\pm0.03\%$ of fucose and $0.6\pm0.3\%$ of neuraminic acid;
(b) a sedimentation coefficient $S_{20,w}^0$ of $4.6\pm0.4$ S;
(c) a molecular weight, determined in polyacrylamide gel containing sodium dodecyl-sulfate (SDS), of $46,000\pm3,000$;
(d) an extinction coefficient $E_1$ $_{cm}^{1\%}$ (280 nm) of $8.82\pm0.5$;
(e) an electrophoretic mobility in the range of albumin and
(f) an isoelectric point of $4.7\pm0.2$.

The characterizing features of the protein are explained as follows:

The sedimentation coefficient was determined in an analytical ultracentrifuge from Messrs. Beckman (Spinco apparatus, Model E) at 60,000 rpm in twin-sector cells at 280 nm using the UV scanner technique. A 0.05 M phosphate buffer (pH 6.8) containing 0.2 mole/l of NaCl was used as the solvent. The protein concentration was adjusted to an optical density of about 3. The sedimentation coefficient was converted to the value on the basis of water at 20° C.

A gel with 7.5% of polyacrylamide (PAA) and containing 0.1% of sodium dodecyl-sulfate (SDS) was used to determine the molecular weight in SDS-PAA gel. Human placental lactogen (HPL) and human albumin and aggregates thereof were used as the comparison substance.

To determine the extinction coefficient, the substance was dissolved in distilled water to give a 0.10% solution (weight:volume).

The electrophoretic mobility was determined by the micromodification method in a Microzone R 200 apparatus from Beckman Instruments on cellulose acetate films (Messrs. Sartorius, Göttingen, Federal Republic of Germany) using sodium diethyl barbiturate buffer (pH 8.6).

The carbohydrates were determined by the method described by H. E. Schultze, R. Schmidtberger and H. Haupt, Biochem. Z. 329, 490 (1958).

The aminoacid analysis was carried out by the method of S. Moore, D. H. Spackman and W. H. Stein, Anal. Chem. 30, 1185 (1958), using a Multichrome B liquid chromatograph from Messrs. Beckman. Cystine was determined as cysteic acid after oxidation of the protein with performic acid (S. Moore et al., Anal. Chem., 238, 235 (1963)). The tryptophan content was determined directly by the photometric method of H. Edelhoch, Biochemistry 6, 1948 (1967).

Table 1 contains the result of the aminoacid analysis of $PP_{16}$

TABLE 1

Aminoacid composition of $PP_{16}$

| | Residues per 100 residues | |
|---|---|---|
| | (mol %) | VC %* |
| Lysine | 5.80 | 9.58 |
| Histidine | 2.66 | 9.26 |
| Arginine | 4.35 | 10.18 |
| Aspartic acid | 12.64 | 4.27 |
| Threonine | 4.00 | 9.01 |
| Serine | 6.04 | 5.16 |
| Glutamic acid | 12.54 | 2.42 |
| Proline | 5.37 | 1.57 |
| Glycine | 5.76 | 6.12 |
| Alanine | 6.09 | 6.44 |
| Cystine/2 | 2.34 | 3.57 |
| Valine | 5.48 | 6.16 |
| Methionine | 2.25 | 12.44 |
| Isoleucine | 5.68 | 0.61 |
| Leucine | 7.78 | 3.89 |
| Tyrosine | 4.17 | 3.79 |
| Phenylalanine | 5.93 | 3.96 |
| Tryptophan | 1.05 | 11.42 |

*VC = variation coefficient $PP_{16}$ has the following properties which can be used in a process for isolating this protein by taking measures corresponding to these properties:

(1) It is precipitated with ammonium sulfate from aqueous solutions at pH 7.0 and 30–60% saturation.
(2) It is precipitated with water-soluble acridine bases, for example 2-ethoxy-6,9-diaminoacridine lactate, at pH values between 4 and 9 and at a concentration of the base of 0.2 to 0.8% w/v.
(3) Under euglobulin precipitation conditions, that is to say in dilute salt solution with the pH value adjusted to 5–6, it mostly remains in the supernatant liquor.
(4) On electrophoretic separation at pH 8.0, $PP_{16}$ exhibits a mobility similar to that of albumin.
(5) On gel filtration with Sephadex ®, it behaves like proteins with molecular weights of 20,000 to 70,000.
(6) It can be bonded to weakly basic ion exchangers, such as, for example, DEAE cellulose or DEAE Sephadex, at a conductivity of about 0–2 mS and a pH value of about 7 to 9 and is only eluted again from the ion exchanger when more highly concentrated salt solutions (1–5% NaCl solutions) are used.

The invention furthermore relates to a process for isolating $PP_{16}$ which comprises fractionating a solution containing this protein utilizing the above properties.

Solutions containing $PP_{16}$ are obtained by extraction of organs in which this protein occurs. Mature human placentas such as are found at childbirth are preferably suitable. However, other organs, such as the spleen, stomach or lung, can also be used. The tissue is triturated mechanically and then stirred with water or salt-containing solutions. The tissue residue is centrifuged off. The supernatant liquor contains the soluble tissue proteins.

In addition to ammonium sulfate, other neutral salts usually employed in preparative biochemistry can of course also be used for precipitating the $PP_{16}$. Other than an acridine base, it is also possible to use a water-soluble derivative of a quinoline base, such as are known for protein fractionations, in the context of the process according to the invention. Besides its electrophoretic properties or its molecular weight, other measures which are suitable for separating a protein with the given properties from other proteins can also be used for isolating the protein. The various methods of gel filtration, gel chromatography or ultrafiltration, or the property of $PP_{16}$ of being able to be bonded to weakly basic ion exchangers from dilute buffer solutions and to be eluted again from the exchangers with more lightly concentrated salt solutions can be used for this isolation.

$PP_{16}$ can be isolated by an appropriate combination of the above measures which effect concentration of $PP_{16}$ or separation of this protein from other proteins.

The protein thus isolated by combined methods of fractionation still contains traces of other proteins as impurities. These can be removed with appropriate immuno-adsorbents, that is to say with carrier-bonded antibodies against these concomitant proteins.

The present invention accordingly relates to the individual steps for concentrating $PP_{16}$ and the process for purifying $PP_{16}$ resulting from combination of the concentration measures.

The process for concentration comprises using the methods corresponding to the above properties 1 to 6 or chemical or biochemical preparative equivalents thereof, and ultrapurification employing immuno-adsorbents.

The invention furthermore relates to a process for the preparation of $PP_{16}$ which comprises subjecting a liquid containing this protein to one or more process measures which are known for isolating proteins and in each case isolating the material containing the protein with the $PP_{16}$ features.

Immunochemical methods can be used for detecting and determining $PP_{16}$, for example in a fraction from a separation operation, since $PP_{16}$ has antigenic properties.

The Ouchterlony gel diffusion technique (see, for example, Schultze and Heremans, Molecular Biology of Human Proteins, volume 1, 134) can be used for immunological detection of $PP_{16}$.

An antiserum which can be used for this purpose can be obtained as follows: a polyvalent antiserum with which $PP_{16}$ can be detected is obtained by immunization of rabbits with a $PP_{16}$-containing placental protein fraction [mother liquors from the crystallization of human placental lactogen (HPL) in accordance with the method of H. Bohn, Experientia 27, 1223 (1971)]. This antiserum can be made substantially specific towards the antigen $PP_{16}$ by absorption with normal human serum and those placenta fractions which do not contain $PP_{16}$, or with proteins, for example with HPL.

The pure $PP_{16}$ isolated according to the present invention can be used to prepare monospecific antisera by immunization of animals by known methods.

FIG. 1b shows the immunological reaction of $PP_{16}$ with a specific antiserum from rabbits after resolution in an electrical field in agar-containing gel.

FIG. 1a shows, for comparison, the resolution of the proteins of serum, made visible by their immune reaction with an antiserum from rabbits against human serum (HS).

The detection and determination of $PP_{16}$ by immunological methods is of diagnostic importance:

$PP_{16}$ is a protein which occurs in a relatively high concentration in some organs of the human body (for example placenta, spleen, stomach and lung). Usually, it cannot be detected in blood, that is to say only traces can be detected ($<1$ mg/l). In illnesses associated with disintegration of $PP_{16}$-containing tissue cells, this protein can appear in increased concentration in the serum or in other body fluids, for example urine. The detection and determination of this protein can be used for diagnostic detection of an illness or for monitoring the course of a disease and for controlling the therapy of such an illness.

$PP_{16}$ can thus be used to prepare antisera which can be employed to detect and determine $PP_{16}$.

The invention is illustrated by the following example:

EXAMPLE (A) Extraction of the placentas and fractionation of the extract with Rivanol ®, and ammonium sulfate 1,000 kg of deep-frozen human placentas were comminuted in a cutting mixer and extracted with 1,000 l of 0.4% (w/w) sodium chloride solution. After the tissue residue had been separated by centrifugation, the extract was adjusted to pH 6.0 with 20% (w/w) acetic acid, and 200 l of a 3% (w:w) solution of 2-ethoxy-6,9-diaminoacridine lactate were added, while stirring.

500 l of 2.5% strength (w:w) NaCl solution were added to the precipitate separated by centrifugation, the mixture was stirred for 4 hours and the 2-ethoxy-6,9-diaminoacridine chloride which separated out was centrifuged off. Solid ammonium sulfate was added slowly to the solution, while stirring, until an end concentration of 30% (w/v) was reached, whereupon $PP_{16}$ precipitated together with other proteins. The precipitate was centrifuged off. About 4.5 kg of a moist paste, called fraction A in the following text, were obtained.

(B) Gel filtration on Sephadex G-150

1,500 g of fraction A were dissolved in water and the solution was dialyzed against a 0.01 M tris-HCl buffer (pH 8.0) containing 0.05% of $NaN_3$ (buffer solution 1). The solution which remained was discharged onto a column (60×56 cm) packed with Sephadex G-150 and the column was eluted with buffer solution 1. The eluates were tested with a specific anti-$PP_{16}$ rabbit serum by the Ouchterlony gel diffusion test. The fractions containing $PP_{16}$ were collected and were labelled fraction B.

(C) Chromatography on DEAE cellulose

Fraction B was adsorbed onto DEAE cellulose (10×28 cm column). The column was flushed with buffer solution 1 and eluted with 0.85% (w:v) sodium chloride solution until a precipitate was no longer obtained when the runnings were treated with trichloroacetic acid. The column was then eluted with 5% NaCl solution. The proteins were precipitated from this second eluate by adding ammonium sulfate until the concentration was 30% (w/v). The precipitate was centrifuged off (fraction C).

(D) Euglobulin precipitation

Fraction C was dissolved in water and the solution was dialyzed against buffer solution 1. The solution was adjusted to pH 5.5 by adding 2 N acetic acid, while stirring. The precipitate, which essentially contained only concomitant proteins, was centrifuged off. The proteins in the supernatant liquor were enriched by concentration on an ultrafilter or by precipitation with ammonium sulfate (30% w/v) and were dialyzed against a 0.1 M ammonium bicarbonate buffer (fraction D).

(E) Preparative zone electrophoresis

Fraction D was introduced into an apparatus for preparative electrophoresis such as is described, for example, by N. Heimburger and R. Schmidtberger in Behringwerke-Mitteilungen, volume 43, page 83 et seq., in particular on pages 119–120. The apparatus comprises an horizontal arrangement of carrier electrophoresis in an open trough in which the carrier material is cooled to below 10° C. in order to remove the Joule heat produced during electrophoresis. The carrier material was a substance which is inert towards proteins, advantageously polyvinyl chloride or copolymers thereof, in the form of fine granules. 0:1 M ammonium bicarbonate solution was used as the buffer. The electrophoresis was advantageously carried out at a field strength of 4–6 volts/cm. The protein $PP_{16}$ migrated in the electric field more rapidly than the $\alpha_1$-globulins. The zone containing the new protein was cut out after the resolution and eluted with water. The eluates were then lyophilized or concentrated on an ultrafilter (fraction E).

(F) Ultrapurification of $PP_{16}$ with immuno-adsorbents $PP_{16}$ in fraction E was still contaminated with small amounts of serum proteins (chiefly albumin) and other placental tissue proteins (chiefly human placental lactogen but in addition also $PP_8$ and $PP_{10}$). These concomitant proteins were removed by inverse or negative immuno-adsorption, that is to say with the aid of carrier-bonded antibodies against the proteins still present as impurities (fraction F).

(G) Gel filtration on Sephadex ® G-100

$PP_{16}$ is a relatively unstable protein. During purification, some molecules were converted into higher-molecular weight aggregates and some were converted into low-molecular weight fragments. To separate off these secondary products, fraction F was subjected to gel filtration again on Sephadex G-100. The main fraction with a molecular weight of about 50,000 was separated, dialyzed against water and lyophilized.

What is claimed is:

1. An isolated tissue protein, $PP_{16}$, obtainable by fractionating an aqueous organ extract, the amino acid composition of said tissue protein being:

| Amino Acid | Mole % | Variation Coefficient (%) |
|---|---|---|
| Lysine | 5.80 | 9.58 |
| Histidine | 2.66 | 9.26 |
| Arginine | 4.35 | 10.18 |
| Aspartic acid | 12.64 | 4.27 |
| Threonine | 4.00 | 9.01 |
| Serine | 6.04 | 5.16 |
| Glutamic acid | 12.54 | 2.42 |
| Proline | 5.37 | 1.57 |
| Glycine | 5.76 | 6.12 |
| Alanine | 6.09 | 6.44 |
| Cystine/2 | 2.34 | 3.57 |
| Valine | 5.48 | 6.16 |
| Methionine | 2.25 | 12.44 |
| Isoleucine | 5.68 | 0.61 |
| Leucine | 7.78 | 3.89 |
| Tyrosine | 4.17 | 3.79 |
| Phenylalanine | 5.93 | 3.96 |
| Tryptophan | 1.05 | 11.42 | said tissue protein further having
   (a) a carbohydrate content of $4.3\pm1.6\%$, comprising $3.4\pm1.2\%$ of hexoses, $0.24\pm0.07\%$ of hexosamines, $0.06\pm0.03\%$ of fucose, and $0.6\pm0.3\%$ of neuraminic acid;
   (b) a sedimentation coefficient $S_{20,w}^0$ of $4.6\pm0.4$ S;
   (c) a molecular weight, determined in a polyacrylamide gel containing sodium dodecyl-sulfate, of $46,000\pm3,000$;
   (d) an extinction coefficient $E_1\ _{cm}{}^{1\%}$ (280 nm) of $8.82\pm0.5$;
   (e) an electrophoretic mobility in the range of albumin; and
   (f) an isoelectric point of $4.7\pm0.2$.

2. A tissue protein as claimed in claim 1, wherein said aqueous organ extract is an extract of human placenta, spleen, stomach, or lung.

3. A tissue protein as claimed in claim 1, wherein said aqueous organ extract is an extract of human placenta.

4. A process for concentrating the tissue protein $PP_{16}$ having the following amino acid analysis:

| Amino Acid | Mole % | Variation Coefficient (%) |
|---|---|---|
| Lysine | 5.80 | 9.58 |
| Histidine | 2.66 | 9.26 |
| Arginine | 4.35 | 10.18 |
| Aspartic acid | 12.64 | 4.27 |
| Threonine | 4.00 | 9.01 |
| Serine | 6.04 | 5.16 |
| Glutamic acid | 12.54 | 2.42 |
| Proline | 5.37 | 1.57 |
| Glycine | 5.76 | 6.12 |
| Alanine | 6.09 | 6.44 |
| Cystine/2 | 2.34 | 3.57 |
| Valine | 5.48 | 6.16 |
| Methionine | 2.25 | 12.44 |
| Isoleucine | 5.68 | 0.61 |
| Leucine | 7.78 | 3.89 |
| Tyrosine | 4.17 | 3.79 |
| Phenylalanine | 5.93 | 3.96 |
| Tryptophan | 1.05 | 11.42 | said tissue protein further having
   (a) a carbohydrate content of $4.3\pm1.6\%$, comprising $3.4\pm1.2\%$ of hexoses, $0.24\pm0.07\%$ of hexosamines, $0.06\pm0.03\%$ of fucose, and $0.6\pm0.3\%$ of neuraminic acid;
   (b) a sedimentation coefficient $S_{20,w}^0$ of $4.6\pm0.4$ S;
   (c) a molecular weight, determined in a polyacrylamide gel containing sodium dodecyl-sulfate, of $46,000\pm3,000$;
   (d) an extinction coefficient $E_1\ _{cm}{}^{1\%}$ (280 nm) of $8.82\pm0.5$;
   (e) an electrophoretic mobility in the range of albumin; and (f) an isoelectric point of 4.7±0.2,
which method comprises subjecting a solution containing this protein to at least one of the following measures and obtaining the fraction enriched in $PP_{16}$:
  (a) precipitation with ammonium sulfate in the pH range from 5 to 8 and at 30-60% saturation;
  (b) precipitation with a water-soluble acridine base at a pH value between 4 and 9 and a concentration of 0.2-0.8% (w/v);
  (c) precipitation of concomitant proteins by adjusting the pH value to 5-6 in a dilute salt solution;
  (d) preparative zone electrophoresis at pH 8 and isolation of the fraction having the mobility of albumin;
  (e) gel filtration to obtain proteins in the molecular weight range from 20,000 to 70,000; and
  (f) adsorption onto a weakly basic ion exchanger and elution of the protein.

5. The method of making an antiserum to the protein of claim 1 which comprises immunizing an animal with the protein of claim 1 and recovering serum containing antibodies to said protein.

6. An antiserum made by the method of claim 5.